(12) United States Patent
Peterson

(10) Patent No.: US 8,834,460 B2
(45) Date of Patent: Sep. 16, 2014

(54) MICROWAVE ABLATION SAFETY PAD, MICROWAVE SAFETY PAD SYSTEM AND METHOD OF USE

(75) Inventor: Darion Peterson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1078 days.

(21) Appl. No.: 12/475,082

(22) Filed: May 29, 2009

(65) Prior Publication Data

US 2010/0305560 A1 Dec. 2, 2010

(51) Int. Cl.
 *A61B 18/18* (2006.01)
 *A61B 19/00* (2006.01)
 *A61B 18/00* (2006.01)

(52) U.S. Cl.
 CPC ......... *A61B 19/40* (2013.01); *A61B 2019/4036* (2013.01); *A61B 2018/00023* (2013.01); *A61B 2019/4081* (2013.01)
 USPC .......................................................... 606/33

(58) Field of Classification Search
 CPC ..................... A61B 18/16; A61B 2018/00023; A61B 2018/167; A61B 2018/1869; A61B 19/40; A61B 2019/4036; A61B 2019/4081
 USPC ............... 606/33, 35; 607/152; 600/372, 382; 128/847, 849, 850, 908
 See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,632,127 A | 12/1986 | Sterzer | |
| 4,632,128 A | 12/1986 | Paglione et al. | |
| 4,798,215 A | 1/1989 | Turner | |
| 4,901,738 A | 2/1990 | Brink et al. | |
| 5,097,844 A | 3/1992 | Turner | |
| 5,381,802 A | 1/1995 | Schwartzenfeld | |
| 5,417,210 A | 5/1995 | Funda et al. | |
| 5,972,007 A | 10/1999 | Sheffield et al. | |
| 6,004,333 A | 12/1999 | Sheffield et al. | |
| 6,031,375 A | 2/2000 | Atalar et al. | |
| 6,033,401 A | 3/2000 | Edwards et al. | |
| 6,047,216 A | 4/2000 | Carl et al. | |
| 6,286,512 B1 | 9/2001 | Loeb et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Michael Peffley
*Assistant Examiner* — Thomas Giuliani

(57) ABSTRACT

A microwave ablation safety pad includes a base layer, an electromagnetic shielding layer and a physical protection layer. The base layer is configured to support a cooling medium designed to absorb thermal energy. The electromagnetic shielding layer, adjacent the base layer, includes a faraday shield configured to prevent the generation of electromagnetic fields. The physical protection layer, adjacent the electromagnetic shielding layer, is configured to resist penetration therethrough.

18 Claims, 5 Drawing Sheets

(56) References Cited

U.S. PATENT DOCUMENTS

| | | |
|---|---|---|
| 6,350,276 B1 | 2/2002 | Knowlton |
| 6,375,606 B1 | 4/2002 | Garibaldi et al. |
| 6,471,695 B1 | 10/2002 | Behl |
| 6,603,994 B2 | 8/2003 | Wallace et al. |
| 6,613,047 B2 | 9/2003 | Edwards |
| 6,673,070 B2 | 1/2004 | Edwards et al. |
| 6,690,976 B2 | 2/2004 | Fenn et al. |
| 6,725,080 B2 | 4/2004 | Melkent et al. |
| 6,725,095 B2 | 4/2004 | Fenn et al. |
| 6,802,839 B2 * | 10/2004 | Behl ........................... 606/32 |
| 6,974,463 B2 | 12/2005 | Magers et al. |
| 7,131,445 B2 | 11/2006 | Amoah |
| 7,439,736 B2 | 10/2008 | Meaney et al. |
| 7,467,015 B2 | 12/2008 | Van der Weide |
| 7,565,207 B2 | 7/2009 | Turner et al. |
| 2002/0022836 A1 | 2/2002 | Goble et al. |
| 2004/0097805 A1 | 5/2004 | Verard et al. |
| 2004/0242992 A1 | 12/2004 | Hareyama |
| 2006/0015162 A1 | 1/2006 | Edward et al. |
| 2007/0219546 A1 | 9/2007 | Mody et al. |
| 2007/0293855 A1 | 12/2007 | Silwa, Jr. et al. |
| 2008/0249521 A1 * | 10/2008 | Dunning et al. ............. 606/35 |
| 2008/0300590 A1 * | 12/2008 | Horne et al. ................. 606/35 |
| 2009/0112202 A1 * | 4/2009 | Young ......................... 606/33 |
| 2009/0171341 A1 * | 7/2009 | Pope et al. .................. 606/34 |
| 2009/0234353 A1 * | 9/2009 | McPherson ................. 606/35 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |
| WO | WO2006/105121 | 10/2006 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.

(56) References Cited

OTHER PUBLICATIONS

U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., 'Theoretical Aspects of "Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Geddes et al., "The Measurement of Physiologic Events by Electrical Impedence" Am. J. Mi, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.

(56) References Cited

OTHER PUBLICATIONS

Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . ." Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, OApr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (1 PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite•Element Codes to Model Electrical Heating and Non•Linear Thermal Transport in Biological Media", Proc. ASME HTD-355, 131 (1997).
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.

(56) References Cited

OTHER PUBLICATIONS

European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline, Product Literature, "Light Key: Visualize a Virtual Keyboard. One With No Moving Parts", Nov. 1, 2003, 4 pages.
Esterline, "Light Key Projection Keyboard" 2004 Advanced Input Systems, located at: <http://www.advanced-input.com/aidpdfdownloads/esterlinelightkey>, Sep. 27, 2004.

* cited by examiner

MICROWAVE ABLATION SAFETY PAD, MICROWAVE SAFETY PAD SYSTEM AND METHOD OF USE

BACKGROUND

1. Technical Field

The present disclosure relates to systems, apparatus and methods for performing a medical procedure, wherein a microwave ablation safety pad is used to protect a healthy portion of body tissue during a microwave ablation procedure. More particularly, the present disclosure relates to a microwave ablation safety pad configured to protect the healthy portion of body tissue during the insertion of a tissue penetrating energy delivery device into a target tissue, during the delivery of microwave energy to the target tissue and from a cutting device used during a subsequent resection of the target tissue. Embodiments of a microwave ablation safety pad in accordance with the present disclosure provide a plurality of protective layers to protect a healthy portion of body tissue from the possible effects of physical, thermal and/or electrical contact from a microwave energy delivery device and/or a resection device.

2. Description of Related Art

In one step of a microwave ablation procedure a microwave energy delivery device is positioned in a portion of target tissue. One particular mode of placement includes the use of a tissue penetrating microwave energy delivery device that is positioned in a portion of target tissue by percutaneous insertion. One potential risk of percutaneous insertion occurs when the clinician inserting the percutaneous device overshoots the target tissue and the tip of the percutaneous device makes physical contact with tissue adjacent the target tissue.

The risk of overshoot of a percutaneous device into adjacent tissue becomes particularly relevant when the adjacent tissue is susceptible to damage. For example, accidental insertion into a member of the vascular system (i.e., a vein, artery and/or heart), a portion of the respiratory system (i.e., lung) and/or a portion of the digestive system (i.e., esophagus and/or stomach) may lead to undesirable complications.

Multiple insertions of microwave energy delivery device with a system array or repeated insertions for particular procedures may further exasperate the potential risk, e.g., an organ resection procedure where a plurality of devices are inserted along a resection line in order to facilitate the removal of a portion of the organ.

After the positioning step, microwave energy is delivered to a target tissue. In many procedures, the target tissue is often adjacent a portion of healthy tissue wherein thermal heating and electrical interference from the electromagnetic fields generated by the microwave antenna may unnecessarily transfer additional heat or energy outside a desired target area.

The present disclosure describes a multilayer apparatus configured to isolate healthy tissue from a target tissue thereby preventing physical, thermal and/or electrical contact between the microwave energy delivery device and the electromagnetic fields generated therefrom and the adjacent healthy tissue.

SUMMARY

A microwave ablation safety pad includes a base layer, an electromagnetic shielding layer and a physical protection layer. The base layer is configured to support a cooling medium designed to absorb thermal energy. The electromagnetic shielding layer, adjacent the base layer, includes a faraday shield configured to prevent the transmission of electromagnetic fields. The physical protection layer, adjacent the electromagnetic shielding layer, is configured to resist penetration therethrough.

The base layer of the microwave ablation safety pad may be actively or passively cooled. In an actively cooled pad, the cooling medium of the base layer may include a cooling fluid or a thermoelectric cooling system. The cooling fluid may be selected from the group consisting of saline, water, alcohol, glycine, oil, air and any combination thereof. The thermoelectric cooling system may include a Peltier cooler, a thermoelectric heat pump, a Peltier diode, a Peltier heat pump, a solid state refrigerator, a thermoelectric cooler or any combination thereof. In a passively cooled pad, the cooling medium of the base layer may include a cool polymer or a heat sink.

The faraday shield of the electromagnetic shielding layer may be configured as a thin metallic sheet, a plurality of spaced apart parallel wires or a metallic open mesh structure. The faraday shield may connect to a ground connection. The metallic open mesh structure may include a spacing and/or a shape that is configured to shield electromagnetic fields generated by a microwave antenna that resonates at a resonate frequency. The resonating frequency of the microwave antenna is at least about 915 MHz.

The physical protection layer of the microwave ablation safety pad may include silicon rubber, nylon, polyethylene, polyurethane, polycarbonate, rubber, plastic or a spunbond olefin fiber. The physical protection layer may be configured to withstand a puncture when applied with 5 lbs of force through an 18 gauge needle or to withstand a puncture when applied with 10 lbs of force through a 10 gauge needle.

In another embodiment, a microwave ablation safety pad system includes a microwave ablation safety pad including a base layer, an electromagnetic shielding layer and a physical protection layer, and a ground connection. The base layer is configured to support a cooling medium that absorbs thermal energy. The electromagnetic shielding layer is adjacent the base layer and includes a faraday shield configured to prevent the generation of electromagnetic fields. The physical protection layer is adjacent the electromagnetic shielding layer and is configured to resist penetration. The ground connection is connected to the electromagnetic shielding layer and provides a ground potential.

In yet another embodiment, a microwave ablation safety pad system includes a microwave generator capable of generating a microwave frequency signal, a microwave ablation device and a microwave ablation safety pad. The microwave ablation device includes a microwave antenna configured to resonate and deliver microwave energy to a target tissue. The microwave ablation safety pad is configured to prevent thermal energy generated in the tissue target from conducting to a healthy tissue, to prevent the emanation of electrosurgical fields to healthy tissue and to prevent the microwave ablation device from physically contacting healthy tissue.

DETAILED DESCRIPTION

Detailed embodiments of the present disclosure are described herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
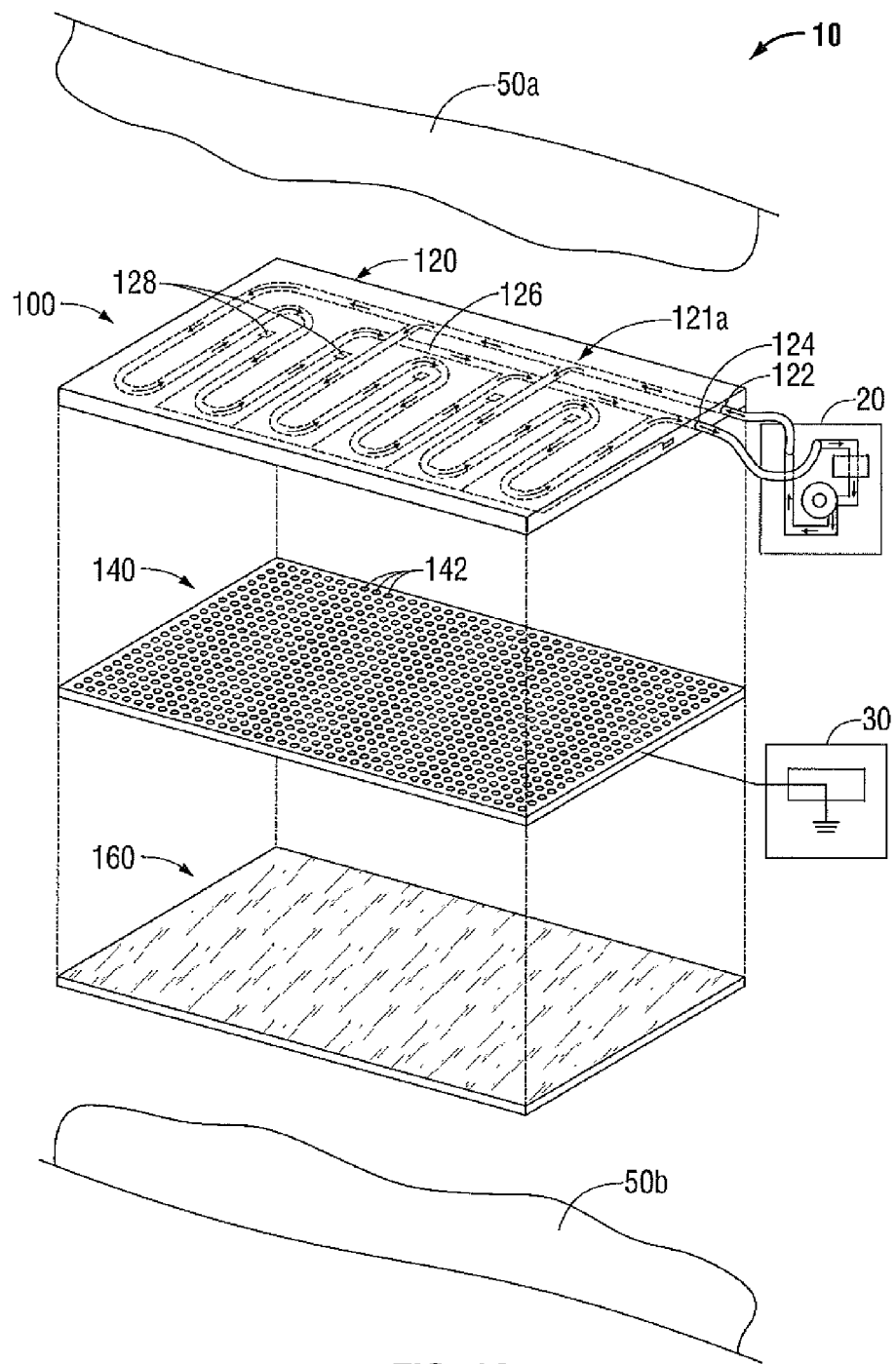
FIG. 1A is a exploded view of a microwave ablation safety pad according to an embodiment of the present disclosure.

Referring to FIG. 1A, a microwave ablation safety pad system employing a microwave ablation safety pad 100 is generally designated as safety pad system 10. Safety pad system 10 includes a microwave ablation safety pad 100, a cooling fluid supply 20 and a grounding device 30. Safety pad system 10 may include individual components, as illustrated in FIG. 1, or the functionality of the individual components may be combined and/or consolidated in one or more components. Components are interconnected with suitable cables, tubes and/or connectors.

Microwave ablation safety pad 100 includes a plurality of protective layers wherein each layer is configured to provide protection to a portion of healthy tissue 50a positioned adjacent a target tissue 50b during a microwave ablation procedure. Microwave ablation safety pad 100 may include a base layer 120, one or more electromagnetic shielding layers 140 and/or physical protection layers 160. The base layer 120 is configured to support one or more cooling mediums designed to absorb thermal energy.

As shown on FIG. 1A, base layer 120 may include an active cooling system 121a configured to actively removes thermal energy from the base layer 120. The active cooling system 121a includes a cooling fluid input 122, a cooling fluid output 124 and a cooling network 126. Cooling fluid input 122 receives a cooling fluid from a suitable cooling fluid supply 20. The cooling network 126 distributes the cooling fluid across the base layer 120 thereby providing a cooled surface to the healthy tissue 50a. In use, cooling fluid circulates through at least a portion of the base layer 120, absorbs thermal energy and exits the base layer 120 through the cooling fluid output 124. Thermal energy is absorbed from the electromagnetic shielding layer 140 and/or the healthy tissue 50a. Cooling fluid outlet 124 may connect to the cooling fluid supply 20 thereby operating as a closed-loop system, as illustrated in FIG. 1. Alternatively, cooling fluid outlet 124 may connect to a suitable fluid drain (not explicitly shown) or to a suitable waste disposal system (not explicitly shown).

Cooling fluid may be selected from the group consisting of saline, water, alcohol, glycine, oil, air or any other suitable cooling medium. Base layer 120 may be selected from the group consisting of plastic or ceramic, such as acrylonitrile butadiene styrene (ABS), polyethylene, polypropylene, zirconium oxide also referred to as zirconia, barium titanate, Sialons (silicon aluminum oxynitride), a cool polymer material, or similar suitable material.

Active cooling system may include a thermoelectric cooling system that uses the Peltier effect to create a heat flux between the junction of two different types of materials. For example, a Peltier cooler or thermoelectric heat pump may transfer heat from one portion of the base layer 120 to another portion of the base layer 120 with consumption of electrical energy. Various devices are know in the art as a Peltier device, a Peltier diode, a Peltier heat pump, a solid state refrigerator, and a thermoelectric cooler (TEC).

Base layer 120 may include one or more sensors 128 that are configured to measure the temperature of the microwave ablation safety pad 100. Sensor 128 may be configured to connect to a microwave generator (not explicitly shown) or to a suitable temperature measuring and/or alarming device (not explicitly shown) configured to measure temperature. The temperature of the base layer 120 may result in the generation of an alarm and/or alert if the measured temperature exceeds a predetermined or selected temperature threshold.

Electromagnetic shielding layer 140 includes a faraday shield and is configured to prevent the penetration of microwave energy and/or the generation of electromagnetic fields in the healthy tissue 50a. The electromagnetic shielding layer 140 may include any suitable faraday shield configurations and constructions such as, for example, a thin sheet of metal, a plurality of spaced apart, parallel wires attached to a common conductor at one end and a metallic open mesh 142, as illustrated in FIG. 1. The electromagnetic shielding layer 140 connects to a suitable ground connection 30, such as, for example, the signal or power ground of the microwave generator, the ground connection of a temperature alarming device or a grounding strap connected to a suitable earth ground.

The construction of the electromagnetic shielding layer 140 may be particularly suited to block and/or absorb energy at a particular frequency. For example, the spacing between the wires in a parallel wire pattern and/or spacing or the mesh size and/or pattern of the metallic open mesh screen may be particularly configured to shield electromagnetic fields generated by a microwave antenna that resonates at a particular resonate frequency, such as, for example, about 915 MHz and 2.45 GHz.

The dimensions and/or the area of the electromagnetic shielding layer 140 may be related to the wavelength of the electromagnetic field that it is intended to shield. For example, the diameter of the electromagnetic shielding layer 140 may be at least equal to the $\lambda/2$, wherein $\lambda$ is equal to the wavelength of the field in air.

Electromagnetic fields in healthy tissue or electrical interference may affect a portion of the nervous system (e.g., the central nervous system (CNS), peripheral nervous system (PNS), etc.). In particular, many procedures that include the delivery of electrosurgical energy to the internal organs of the torso require the placement of electrosurgical instruments near a portion of the spinal cord of the CNS or a portion of the autonomic nervous system of the PNS that controls the internal organs, blood vessels, smooth and cardiac muscles. Unnecessary or prolonged exposure to electromagnetic fields or electrical interference may result in damage to the structure and/or the function of the nervous system. This is particularly important when the target tissue is positioned relative sensitive tissue areas, e.g. spinal cord.

The physical protection layer 160 is a robust layer configured to prevent sharp surgical instruments, such as ablation probes or temperature probes, from penetrating therethrough. Physical protection layer 160 may be formed from a flexible material, such as, for example, silicone rubber, wherein the flexible material prevents penetration of a sharpened tip without damaging or deforming the tip structure of the device. Other suitable materials include nylon, polyethylene, polyurethane, polycarbonate, rubber, plastic and a spunbond olefin fiber such as the material manufactured by Dupont of Wilmington, Del., and sold under the trademark of Tyvek®.

Physical protection layer 160 may be integrally formed into, or as part of, the electromagnetic shielding layer 140. In one embodiment, the physical protection layer 160 may be a coating formed on the electromagnetic shielding layer 140. In another embodiment, the electromagnetic shielding layer 140, such as a parallel wire pattern or open mesh, may be enclosed within the physical protection layer 160.

Physical protection layer 160 may also form an insulative barrier between the heat generated in the target tissue 50b and the base layer 120 of the microwave ablation safety pad 120. The removal of thermal energy from the target tissue 50b may compromise the microwave energy ablation procedure by creating inconsistent heating patterns or not achieving a target temperature in at least a portion of the target tissue. As such, the physical protection layer 160 may be configured to alleviate this issue by preventing thermal energy from conducting from the target tissue 50b to the base layer 120 thereby allowing the base layer 120 to cool the healthy tissue 50a without compromising the ablation or resection procedure.

In one embodiment, the physical protection layer 160 is configured to make contact with the sharpened tip of a percutaneous microwave ablation device (while preventing the tip from penetrating therethrough) without damaging or deforming the sharpened tip portion of the ablation device. The physical protection layer 160 is sufficiently strong to prevent the clinician from advancing the sharpened tip of the ablation probe into or through the microwave ablation safety pad 100. For example, the physical protection layer may withstand puncture from about 5-10 lbs of force applied with a 18-10 gage needle.

The strength of the physical protection layer 160 may be particularly suited for the procedure in which the microwave ablation safety pad 100 is used. For example, the strength may be based on the size of the ablation probe, the tissue in which the procedure is performed, the amount of tissue in which the ablation probe must penetrate and the conditions under which the procedure is performed (e.g., percutaneously through the skin or during an open surgical procedure).

Figure 1B:
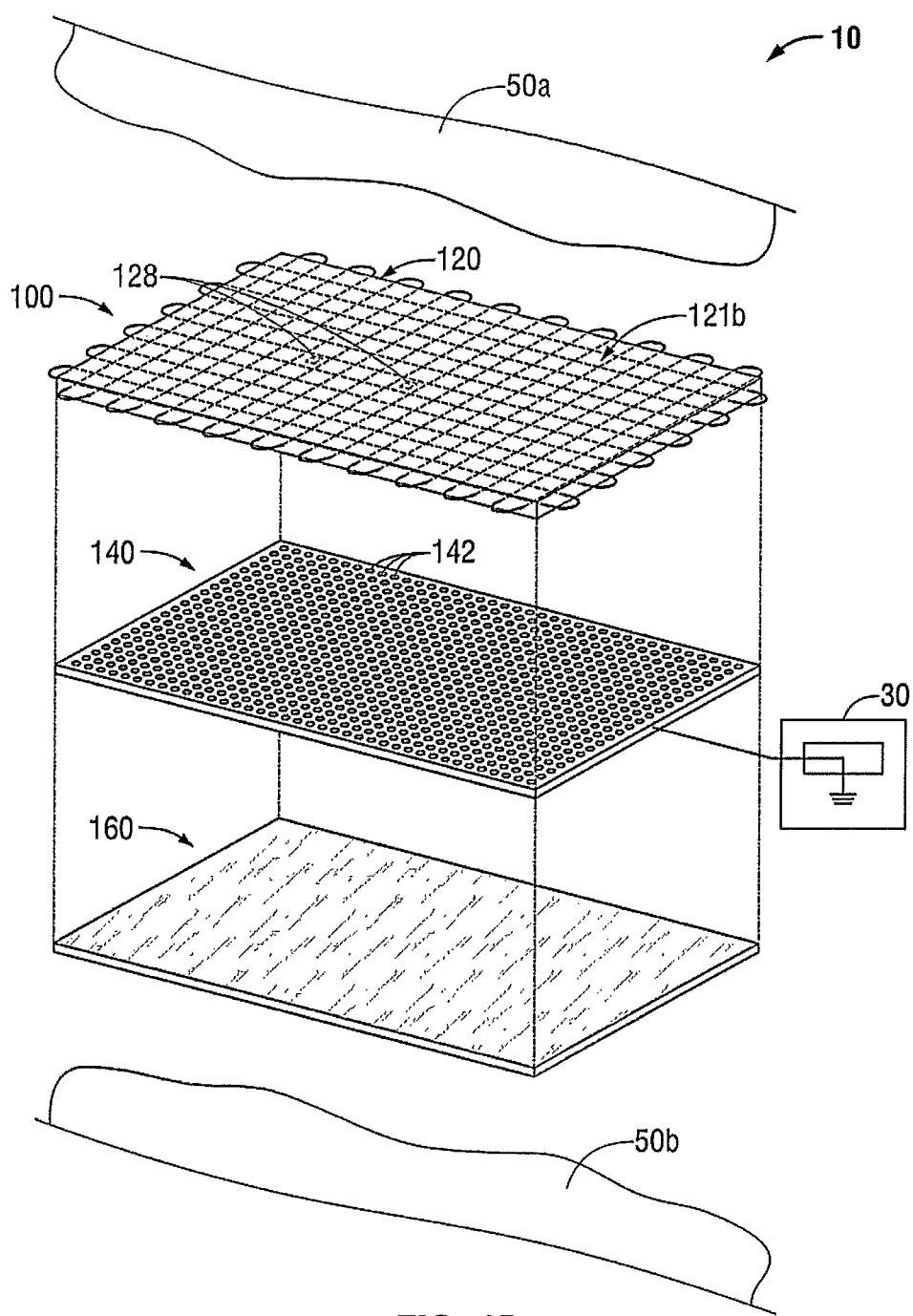
FIG. 1B is an exploded view of a passively cooled microwave ablation safety pad according to another embodiment of the present disclosure.

As shown on FIG. 1B, cooling medium of the base layer 120 may include a passive cooling system 121b configured to passively removes thermal energy from the base layer 120 and/or reduce thermal spread to the healthy tissue. Passive cooling system 121b may include a network of heat conductive members configured to conduct thermal energy to the periphery of the base layer 120. Passive cooling system 121b may include a heat sink, heat dissipating fins, a heat dissipation material, a Cool polymer and/or other passive cooling solutions which are known to effectively control thermal spread. Some of these techniques are disclosed in commonly-owned U.S. Pat. No. 7,147,638 to Chapman et al and U.S. patent application Ser. No. 11/184,338 to Chapman, herein incorporated by reference. Thermal energy is absorbed from the electromagnetic shielding layer 140 and/or the healthy tissue 50a.

A Cool polymer material is a thermally conductive, electrically insulative material that acts as heat sinks (i.e., absorb heat) during the energy delivery period of the procedure thereby limiting thermal spread to adjacent healthy tissue. Examples of Cool polymers include thermally conductive plastic materials which dissipate heat in a more isothermal profile to the surrounding environment resulting in a lower maximum temperature and reduced formation of hot spots such as materials commonly sold under the trademark CoolPoly® by Cool Polymers, Inc., of Rhode Island. In one embodiment the network of heat conductive members may be formed from Cool polymers disposed within at least a portion of the base layer wherein the cool polymer propagates thermal energy away from the healthy tissue.

Figure 2A:
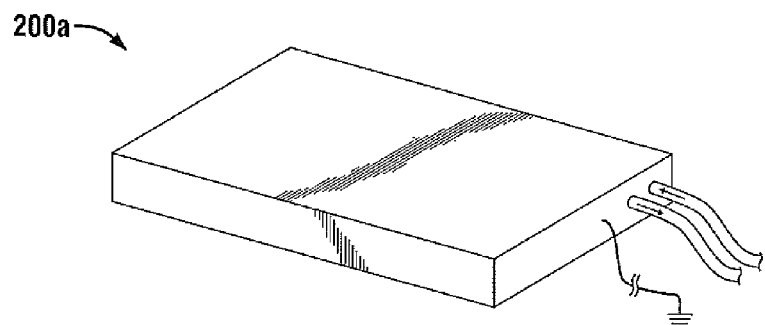
FIGS. 2A-2C are illustrations of microwave ablation safety pads of various shapes with the structure of the microwave ablation safety pad of FIG. 1.
Figure 2B:
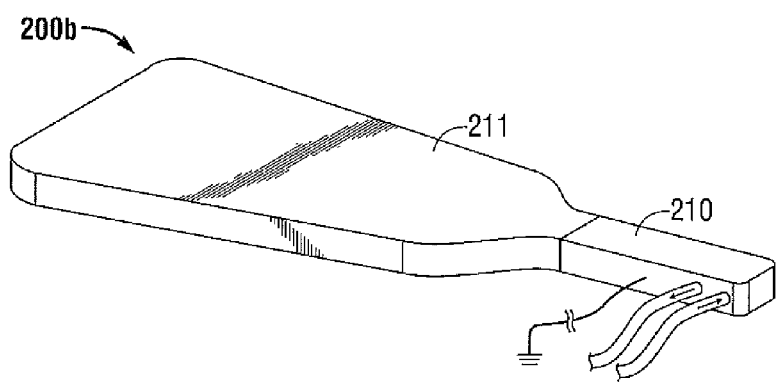
Figure 2C:
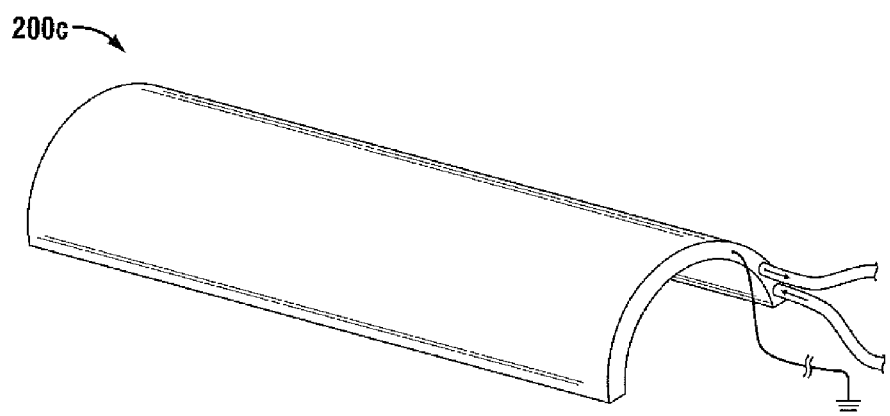

The microwave ablation safety pad of the present disclosure may form any suitable shape as illustrated in FIGS. 2A-2C. In FIG. 2A, the microwave ablation safety pad 200a is rectangular shaped. In FIG. 2B, the microwave ablation safety pad 200b is paddle shaped with a handle 210 and a face 211. Handle 210 may be configured to support the paddle portion thereby allowing manipulation of the microwave ablation safety pad 200b into a suitable position. In FIG. 2C, the microwave ablation safety pad 200c is tubular shaped and configured to partially surround and protect a tubular body structure, as discussed herein below.

Figure 3A:
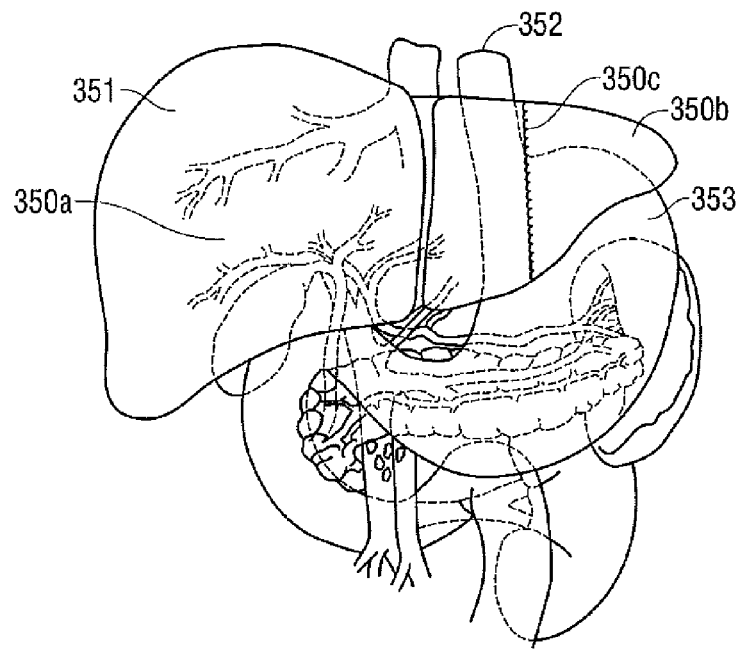
FIGS. 3A-3D illustrate the steps of a resection procedure using a microwave ablation safety pad according to a method of the present disclosure.

FIGS. 3A-3D illustrate the steps of a tissue resection procedure using a microwave ablation safety pad 300. FIG. 3A is an illustration of the various internal organs in a human torso, in particular the liver 351, the esophagus 352 and the stomach 353. In this particular example, the liver includes a healthy liver portion 350a and an unhealthy liver portion 350b. The steps describe a medical procedure wherein the unhealthy liver portion 350b is resected from the healthy liver portion 350a at a predetermined resection line 350c. The esophagus 352 and stomach 353 are adjacent the resection line 350c and are therefore at risk of injury during the insertion step, the ablation step and/or the resection step.

Figure 3B:
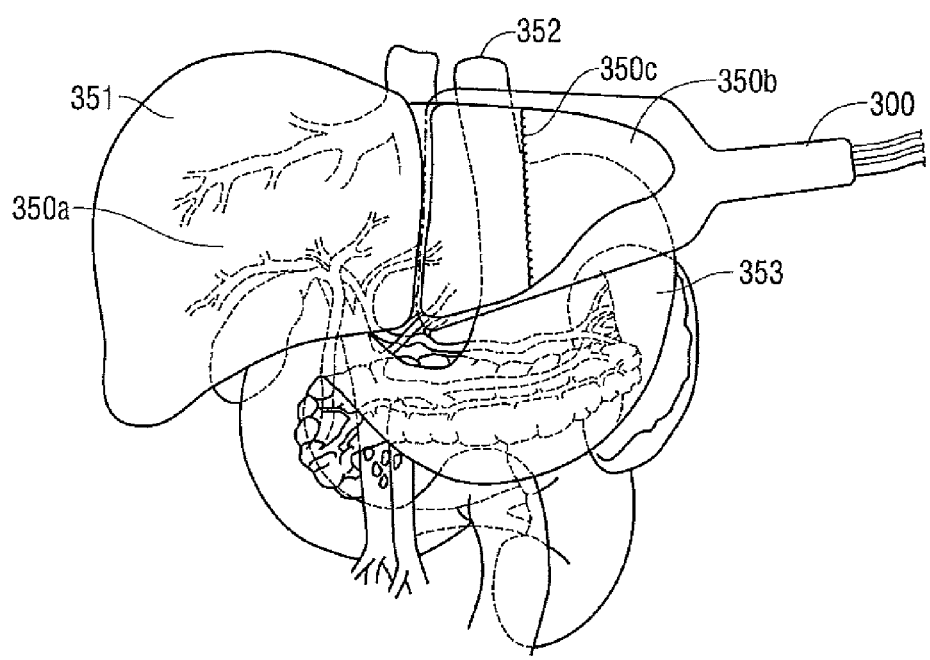

During the insertion step, the clinician inserts one or more percutaneous microwave ablation devices along the resection line 350c. To determine the position and insertion depth of the ablation device the clinician may use one or more suitable monitoring devices or methods such as, for example, an ultrasonic or optical imaging device, a depth guide or an insertion gauge. Even with a suitable monitoring device, penetration beyond the target depth and into or through adjacent healthy tissue (e.g., stomach 353 and esophagus 352) is still a potential risk. To minimize (or eliminate) this potential risk, a microwave ablation safety pad 300 may be positioned between the target tissue 350b/resection line 350c and the adjacent healthy tissue 352, 353, as illustrated in FIG. 3B.

The microwave ablation safety pad 300 may be particularly shaped for a specific ablation procedure or to conform to a specific organ. For example, the microwave ablation safety pad 300 in FIG. 3B is particularly shaped for an ablation procedure or resection procedure on the left liver lobe. In another example, the microwave ablation safety pad 200c of FIG. 2C is particularly shaped to protect a tubular body portion such as, for example, the esophagus, the spine, an elongated vein or artery such as the superior vena cava or the abdominal aorta. The features of a microwave ablation safety pad of the present disclosure may be particularly suited to any shape and therefore the specific embodiments described herein should not be construed as limiting.

Figure 3C:
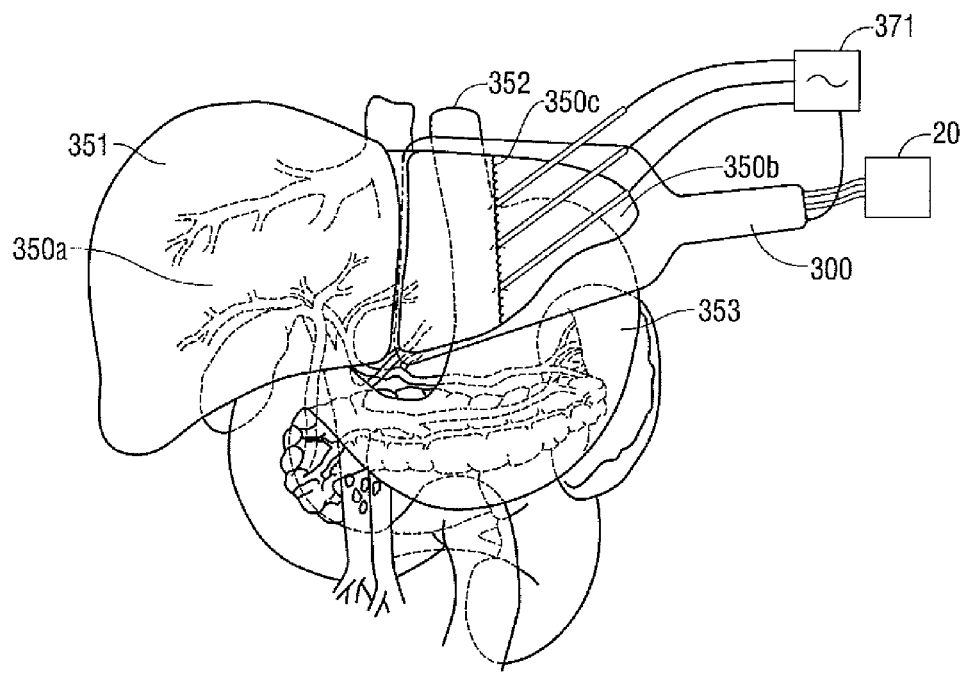

FIG. 3C illustrates a plurality of microwave ablation probes 370a, 370b, 370c percutaneously inserted along the resection line 350c and connected to a microwave generator 371 capable if generating and supply a microwave energy signal for the particular ablation/resection procedure. In one method of percutaneously inserting an ablation probe, the clinician inserts the probe completely through the unhealthy liver portion 350b such that the ablation probe makes contact with the microwave ablation safety pad 300. After making contact with the microwave ablation safety pad 300 the clinician partially withdraws the ablation probe a predetermined amount thereby resulting in proper and/or consistent placement.

Base layer (not explicitly shown) of the microwave ablation safety pad 300 connects to a cooling fluid supply 20 that provides cooling fluid thereto. Cooling fluid supply 20 may also be configured to provide cooling fluid to one or more of the microwave ablation probes 370a, 370b, 370c. Cooling fluid, after circulating though the microwave ablation safety pad 300 and the microwave ablation probes 370a, 370b, 370c is discharged to a fluid drain or returned to the cooling fluid supply 20, as illustrated in FIG. 3C.

The electromagnetic shielding layer (not explicitly shown) of the microwave ablation safety pad 300 is adequately grounded through the microwave generator 371 or to a suitable ground potential. During delivery of the microwave energy signal to the microwave ablation probes 370a, 370b, 370c the healthy tissue 352, 353 is protected from the electromagnetic heating by the electromagnetic shielding layer.

Figure 3D:
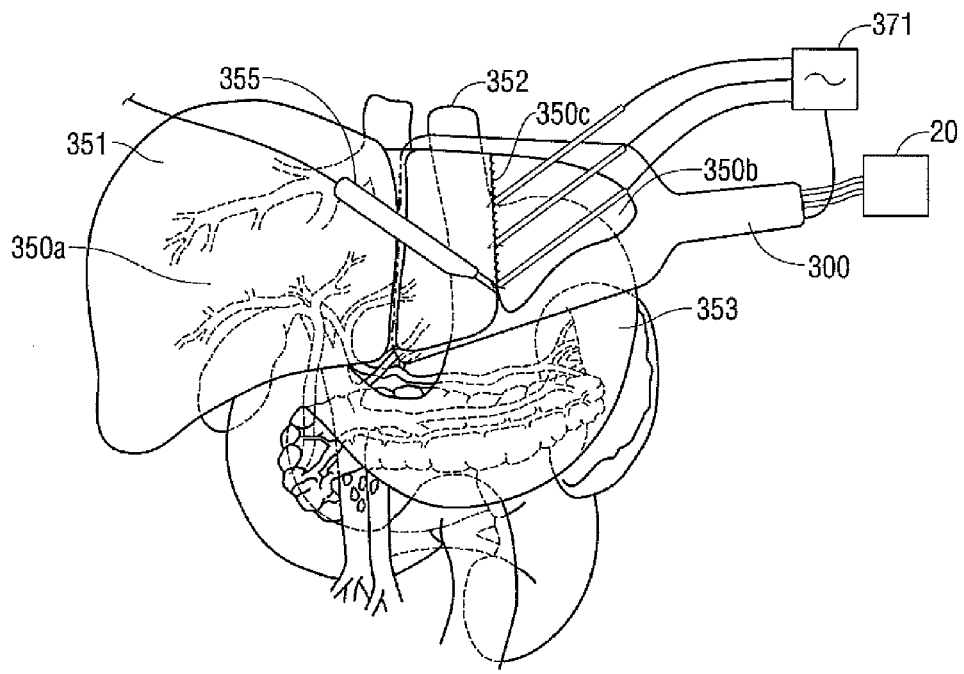

After the resection line 350c is adequately ablated the unhealthy liver portion 350b is resected from the healthy liver portion 350a as illustrated in FIG. 3D. The resection may be performed with any suitable surgical cutting device 355 such as, for example, a scalpel and an electrosurgical cutting apparatus. During resection, the microwave ablation safety pad 300 protects the healthy tissue 352, 353 from physical contact with the cutting device 355 and from electrosurgical energy or electrosurgical currents that may be generated by an electrosurgical cutting apparatus.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A microwave ablation safety pad system, comprising a microwave generator capable of generating a microwave frequency signal; at least one microwave ablation device, including a microwave antenna and a sharpened tip on a distal end thereof, the microwave antenna configured to resonate and deliver microwave energy to a target tissue, and a microwave ablation safety pad including:
    a base layer configured to support a cooling medium designed to absorb thermal energy;
    an electromagnetic shielding layer adjacent the base layer, the electromagnetic shielding layer including a faraday shield configured to prevent the transmission of electromagnetic fields; and
    a physical protection layer adjacent the electromagnetic shielding layer, the physical protection layer configured to prevent advancement of the sharpened tip therethrough.

2. The microwave ablation safety pad system of claim 1, wherein the base layer is actively cooled.

3. The microwave ablation safety pad system of claim 2, wherein the cooling medium includes cooling fluid.

4. The microwave ablation safety pad system of claim 3, wherein the cooling fluid is selected from the group consisting of saline, water, alcohol, glycine, oil and air.

5. The microwave ablation safety pad system of claim 2, wherein the base layer includes a thermoelectric cooling system.

6. The microwave ablation safety pad system of claim 5, wherein the thermoelectric cooling system is selected from a group consisting of a Peltier cooler, a thermoelectric heat pump, a Peltier diode, a Peltier heat pump, a solid state refrigerator, and a thermoelectric cooler.

7. The microwave ablation safety pad system of claim 1, wherein the base layer is passively cooled.

8. The microwave ablation safety pad system of claim 7, wherein the base layer includes a cool polymer.

9. The microwave ablation safety pad system of claim 7, wherein the base layer includes a heat sink.

10. The microwave ablation safety pad system of claim 1, wherein the faraday shield of the electromagnetic shielding layer is configured as one of a thin metallic sheet, a plurality of spaced apart parallel wires and a metallic open mesh structure.

11. The microwave ablation safety pad system of claim 10, wherein the faraday shield of the electromagnetic shielding layer connects to a ground connection.

12. The microwave ablation safety pad system of claim 1, wherein the faraday shield of the electromagnetic shielding layer is a metallic open mesh structure wherein the spacing and shape of the metallic open mesh structure is configured to shield electromagnetic fields generated by the microwave antenna that resonates at a resonate frequency.

13. The microwave ablation safety pad system of claim 12, wherein the faraday shield of the electromagnetic shielding layer connects to a ground connection.

14. The microwave ablation safety pad system of claim 12, wherein the resonate frequency of the microwave antenna is at least about 915 MHz.

15. The microwave ablation safety pad system of claim 1, wherein the physical protection layer includes at least one of silicon rubber, nylon, polyethylene, polyurethane, polycarbonate, rubber, plastic and a spunbond olefin fiber.

16. The microwave ablation safety pad system of claim 15, wherein the physical protection layer is configured to withstand a puncture when applied with 5 lbs of force through an 18 gauge needle.

17. The microwave ablation safety pad system of claim 15, wherein the physical protection layer is configured to withstand a puncture when applied with 10 lbs of force through a 10 gauge needle.

18. A microwave ablation safety pad system comprising a microwave generator capable of generating a microwave frequency signal; at least one microwave ablation device, including a microwave antenna and a sharpened tip on a distal end thereof, the microwave antenna configured to resonate and deliver microwave energy to a target tissue, and
    a microwave ablation safety pad including:
        a base layer configured to support a cooling medium designed to absorb thermal energy;
        an electromagnetic shielding layer adjacent the base layer, the electromagnetic shielding layer including a faraday shield configured to prevent the generation of electromagnetic fields; and
        a physical protection layer adjacent the electromagnetic shielding layer, the physical protection layer configured to prevent advancement of the sharpened tip of the microwave antenna therethrough; and
        a ground connection connected to the electromagnetic shielding layer and providing a ground potential thereto.

* * * * *